United States Patent [19]

Stone

[11] Patent Number: 4,884,562
[45] Date of Patent: Dec. 5, 1989

[54] SUSPENSION BRACE ASSEMBLY

[76] Inventor: Mario M. Stone, 333 Arthur Godfrey Rd., Miami Beach, Fla. 33140

[21] Appl. No.: 945,178

[22] Filed: Dec. 22, 1986

Related U.S. Application Data

[63] Continuation of Ser. No. 740,654, Jun. 3, 1985, abandoned.

[51] Int. Cl.⁴ .............................................. A61F 5/02
[52] U.S. Cl. ........................................ 128/78; 128/68
[58] Field of Search ............ 128/78, 68, 92 Z, 92 ZZ, 128/92 YM, 518 B, 518 R, 538, 541, 546, 567, 570

[56] References Cited

U.S. PATENT DOCUMENTS

| | | | |
|---|---|---|---|
| 2,181,689 | 11/1939 | Bell | 128/78 |
| 3,570,480 | 3/1971 | Stubbs | 128/78 |
| 3,926,183 | 12/1975 | Spiro | 128/78 |
| 4,022,197 | 5/1977 | Castiglia | 128/78 X |
| 4,099,524 | 7/1978 | Cueman et al. | 128/78 |
| 4,175,553 | 11/1979 | Rosenberg | 128/78 |
| 4,245,628 | 1/1981 | Eichler | 128/78 |
| 4,325,363 | 4/1982 | Berkeley | 128/78 X |
| 4,459,979 | 7/1984 | Lewis, Jr. | 128/78 |

Primary Examiner—Edgar S. Burr
Assistant Examiner—Moshe I. Cohen
Attorney, Agent, or Firm—Roylance, Abrams, Berdo & Goodman

[57] ABSTRACT

A suspension type brace designed to be worn on and surround a portion of the human body in the region of the lower back. The brace assembly comprises two spaced apart lateral support assemblies each incorporating specifically configured brace structures having sufficient rigidity to restrict lateral bending of the torso and lateral flexion-extension and rotation of the lumbosacral portion of the spine while allowing forward bending of the torso.

7 Claims, 1 Drawing Sheet

SUSPENSION BRACE ASSEMBLY

This application is a continuation of Ser. No. 740,654, filed June 3, 1985, now abandoned.

BACKGROUND OF THE INVENTION

1. Field of the Invention

The present invention is directed towards a brace assembly specifically structured to stabilize the lumbosacral portion of the spine by defining a suspension mechanism through the disposition of spaced apart lateral support assemblies surrounding the sides of the torso in the area of the lower back and disposed between and in engaging relation with the lower portion of the ribs, at the upper end thereof, and the iliac crest and greater trochanter at the lower end thereof.

2. Description of the Prior Art

Medical advances in the area of body worn braces has advanced to the point where a very large number of brace structures exist and are commercially available which are specifically designed to alleviate pain by restricting movement and providing support to various portions of the body. A common malady to which prior art brace structures have been applied is the reduction of pain and stress in the lower back or lumbar spine area. The majority of the prior art brace assemblies attempt to stabilize certain portions of the spinal column by restricting movement which in turn restricts motions that cause pain in the facet joints as they rotate or subluxate laterally.

However, certain problems associated with prior art brace structures include extensive restriction of movement in any direction of the braced or surrounded portion of the torso in an attempt to maintain the spine, or other affected portion of the body, in a stabilized position. For example, patients wearing a number of prior art standard braces have difficulty in performing normal every day activities such as sitting, driving an automobile, or bending forward. Such prior art braces of the type referred to frequently are overly complex, heavy and uncomfortable especially when the patient is forced to wear such brace structures for prolonged periods.

Accordingly, there is a need in the area of brace assemblies for a structure which efficiently alleviates lower back pain through the stabilization of the lumbosacral portion of the spine through the restriction of lateral bending of the torso and the attendant restriction of lateral flexion-extension and rotation of the affected area of the spine.

SUMMARY OF THE INVENTION

The present invention relates to a brace assembly of the type to be worn on the body and which is specifically structured to define a suspension mechanism for the purposes of stabilizing the lower or lumbosacral region of the spine in order to reduce low back pain during acute lumbar spine pain syndromes. The structural design of the subject brace assembly is based on the fact that by limitation of the side bending of the torso and the attendant limitation of side or lateral flexion of the lumbar spine, rotation of the spine is also controlled thus avoiding facet tendency to subluxation and therefore ligamentous strain. The subject brace assembly limits side bending and therefore attendant secondary rotation. This is accomplished through the provision of two spaced apart lateral brace assemblies mounted on a foundation. The foundation of the subject brace assembly has a sufficient longitudinal dimension to surround the torso in the area of the lower back.

The spaced apart lateral support assemblies each include a brace structure being disposed and having sufficient rigidity to restrict the lateral bending of the torso. This restriction in turn limits the lateral flexion-extension and attendant rotation of the lumbosacral spine.

Torsion may be defined as a force applied tending to rotate or twist a bar or like elongated element about its longitudinal axis. Torsion stresses in the spine are produced by twisting forces, i.e., forces applied tend to rotate the spine about this longitudinal axis. When such forces are applied at any vertebra level, that level tends to rotate about the next adjacent lower vertebra level. Suspension of the lumbar spine decreases the actual load on the intervertebral discs. A force is applied to the spine in an attempt to restore the individual segments to their original shape and position. It is a force applied in tension. (suspension). The person's trunk or torso is not purely squeezed or stretched but tends to rotate or bend. Torsion stresses in the spine are produced by twisting forces, i.e., forces applied that tend to rotate the spine about its longitudinal axis. As set forth above, when such torsional stresses are subjected to the spine at any vertebral level, that level tends to rotate about and relative to the next adjacent lowest vertebral level. Adequate bracing of the lumbosacral spine must limit both flexion-extension and lateral tilt if it is to sufficiently immobilize that interspace.

In order to accomplish the above, the brace structures associated with each of the spaced apart lateral support assemblies collectively define a suspension mechanism by the engagement of the upper longitudinal end of each lateral support assembly with the lower rib portions on each side of the torso. In addition, the lower longitudinal end of each lateral support assembly rests on the iliac crest and greater trochanter thus producing an effective suspension of the lumbosacral spine.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
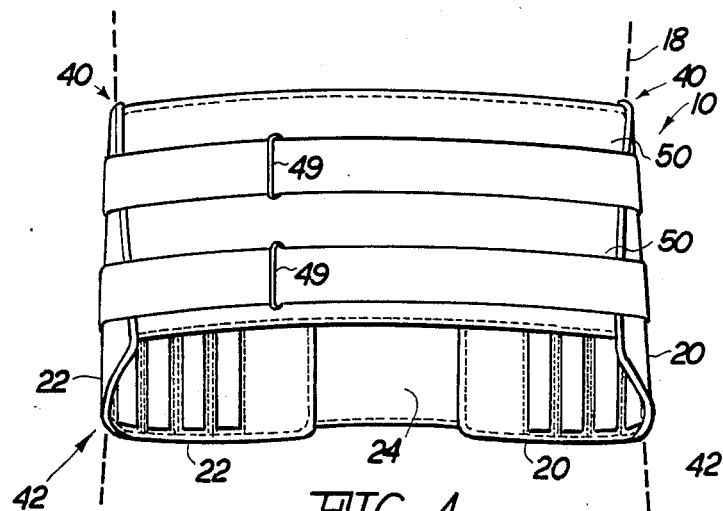
FIG. 1 is a front plan view of the brace assembly of the present invention disposed in mounted, surrounding relation about the torso (represented in broken lines) of the wearer of the brace assembly.

As shown in FIGS. 1 through 4, the brace assembly of the present invention is generally indicated as 10 and comprises a foundation 12 having an elongated configuration and sufficient longitudinal dimension between opposite ends generally indicated as 14 and 16 (FIG. 3) to surround an intended portion of a torso represented in broken lines as 18 in FIG. 1.

The foundation further includes a trochanteric pad including spaced apart lateral support assemblies 20 and 22 interconnected by a panel 24 which is preferably formed from an elastic material. The elastic material panel allows some relative displacement of the respective lateral support assemblies 20 and 22 upon movement of the torso. However, an important structural feature of the present invention is the provision of a bracing structure formed of rigid material and mounted within each of the assemblies 20 and 22 wherein the bracing structure of each lateral support assembly 20 and 22 is disposed and dimensioned to restrict lateral bending of the torso when it is surrounded by the subject brace assembly 10.

Figure 2:
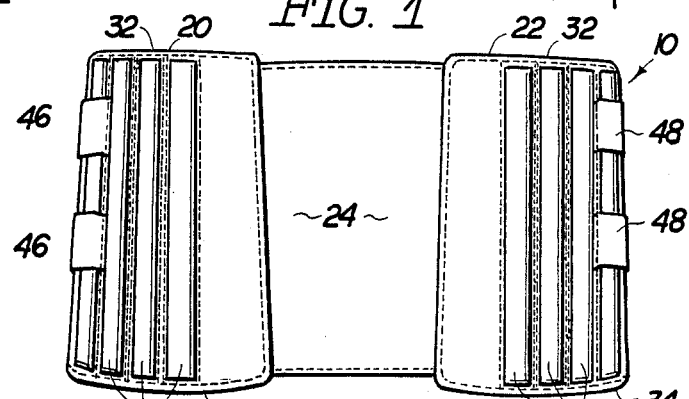
FIG. 2 is a rear plan view of the embodiment of FIG. 1.
Figure 3:
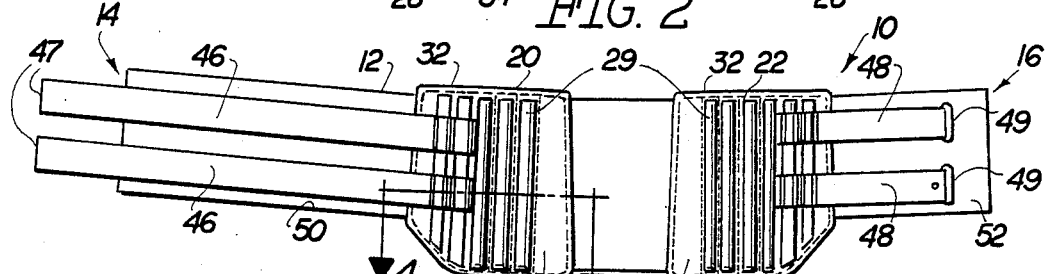
FIG. 3 is a rear plan view of the subject brace assembly in an outwardly extended and substantially planar orientation.
Figure 4:
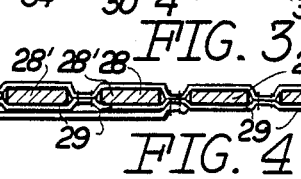
FIG. 4 is a sectional view along line 4—4 of FIG. 3 showing structural details of the foundation, cover and bracing structure of the present invention.

More specifically, the brace structure associated with each brace assembly comprises, in a preferred embodiment, a plurality of brace elements 28 formed from a rigid material such as but not limited to aluminum and which effectively extends along the entire transverse dimension as clearly shown in FIGS. 2 and 3 of each of the respective lateral support assemblies 20 and 22.

Each of the brace elements 28 is housed within one of a plurality of pockets 29 disposed in spaced apart and substantially segregated relation to one another. The pockets 29 extend along the entire length and have substantially the same longitudinal dimension as the brace elements 28 maintained on the interior thereof. Further, the pockets 29 are part of a cover means 30 formed from a non-irritating material such as hyperallergenic felt which surrounds the plurality of brace elements and further which allows their at least partially surrounding disposition relative to the sides of the torso 18 in the area of the lumbar spine as clearly shown in FIG. 1. In order to accomplish proper support and in order to further define a suspension mechanism, a plurality of the brace elements 28' have a varied longitudinal dimension relative to the remainder of the brace elements 28 (see FIG. 4). This allows the oppositely disposed upper and lower longitudinal ends 32 and 34 of each support assembly 20 and 22 to define the periphery of the respective lateral support assemblies and provide rigid bracing at these oppositely disposed spaced apart longitudinal ends 32 and 34.

The transverse dimension of each of the lateral support assemblies 20 and 22 is substantially the same, allowing for certain overlapping tolerances of the cover means 30, as the longitudinal dimension of the respective brace elements 28 and 28'. Accordingly, the upper longitudinal end 32 of each support assembly 20 and 22 has a substantially straight line configuration and the lower longitudinal end 34 of each support assembly 20 and 22 has an angular upwardly inclined configuration or orientation extending from the lower longitudinal end 36 to approximately the respectively positioned belts 50 and 52. Further, the transverse dimension of each lateral support assembly 20 and 22 (being equal to the longitudinal dimension of the respective brace elements 28 and 28') may be varied dependent upon the overall size of the torso on which the brace is to be applied. The relative dimensions must be such that the upper end 32 of each lateral support assembly engages the lower portion of the ribs in the general vicinity 40 as that shown in FIG. 1. Similarly, the lower longitudinal end 34 is positioned to engage the iliac crest and greater trochanter in the general vicinity 42 as indicated in FIG. 1. A suspension mechanism is thereby defined which applies tension or elongated forces to the lumbosacral spine since the trochanteric pad is effectively perched in suspending relation between the lower rib portion at the upper longitudinal end thereof and the iliac crest and greater trochanter at the lower longitudinal end thereof. Further, due to the disposition and rigidity of the plurality of bracing elements as shown in FIGS. 1 and 2, adequate bracing of the lumbosacral spine is provided which limits both flexion-extension and rotation thereof through the restriction of lateral bending or tilting of the torso.

Other structural features of the present invention include a connecting means including at least one and preferably a plurality of straps 46 extending outwardly from one of the lateral support assemblies 20 wherein each of the straps 46 has a free end 47. Similarly, the connecting means includes a similar number of straps 48 extending outwardly from lateral support assembly 22 and having a buckle or like connector 49 affixed to the opposite ends thereof for attachment with the free ends 47 of the opposing straps 46 of the connecting means. Overlapping belts 50 and 52 are provided to insure a snug surrounding engagement of the foundation 12 including trochanteric pad in the designated and intended portions of the torso in the area of the lower back.

What is claimed is:

1. A suspension brace assembly for supporting and stabilizing the lumbosacral portion of the spine of a wearer by suspending the wearer's spine and restricting lateral bending of the wearer's torso, the combination comprising:

a foundation for surrounding the wearer's torso about the area of the lower back;

means, coupled to said foundation, for tightening said foundation about the wearer's torso; and first and second lateral support assemblies coupled to said foundation and spaced laterally along said foundation at positions to engage the side portions of the wearer's torso for suspending the wearer's spine and for restricting lateral bending of the lumbosacral portion of the wearer's spine, each of said first and second lateral support assemblies including a plurality of substantially rigid brace elements, each of said brace elements having a length sufficient for suspending the wearer's spine by applying tension forces thereto, and having an upper end engaging lower ribs of the wearer and a lower end engaging the iliac crest and greater trochanter of the wearer's torso to suspend the lower portion of the wearer's spine and to restrict lateral bending of the lumbosacral portion of the wearer's spine.

2. A suspension brace assembly according to claim 1, wherein said foundation includes an elastic panel interconnecting said first and second lateral support assemblies and disposed in overlying relation to the lower back of the wearer's torso.

3. A suspension brace assembly according to claim 2, wherein
said foundation includes a front portion disposed substantially opposite said elastic panel when positioned on the wearer's torso.

4. A suspension brace assembly according to claim 2, wherein
said elastic panel is free of any rigid bracing means.

5. A suspension brace assembly according to claim 1, wherein
each of said first and second lateral support assemblies further comprises a cover disposed thereon.

6. A suspension brace assembly according to claim 1, wherein
each of said first and second lateral support assemblies includes upper and lower longitudinal ends defining peripheral portions with said upper longitudinal ends having a substantially straight line configuration for engaging the wearer's ribs.

7. A suspension brace assembly according to claim 1, wherein
said means for tightening includes a plurality of straps.

* * * * *